US009992409B2

(12) United States Patent
Anzue et al.

(10) Patent No.: US 9,992,409 B2
(45) Date of Patent: Jun. 5, 2018

(54) DIGITAL MIRROR APPARATUS

(71) Applicant: Panasonic Intellectual Property Management Co., Ltd., Osaka (JP)

(72) Inventors: Naomi Anzue, Osaka (JP); Michihiro Yamagata, Osaka (JP); Norihiro Imamura, Osaka (JP); Yoshimitsu Noguchi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days. days.

(21) Appl. No.: 14/765,587

(22) PCT Filed: Feb. 14, 2014

(86) PCT No.: PCT/JP2014/000758
§ 371 (c)(1),
(2) Date: Aug. 4, 2015

(87) PCT Pub. No.: WO2014/125831
PCT Pub. Date: Aug. 21, 2014

(65) Prior Publication Data
US 2015/0373264 A1    Dec. 24, 2015

(30) Foreign Application Priority Data
Feb. 14, 2013    (JP) ................... 2013-026504

(51) Int. Cl.
*H04N 5/222*    (2006.01)
*G09G 5/00*    (2006.01)
(Continued)

(52) U.S. Cl.
CPC ....... *H04N 5/23232* (2013.01); *A61B 5/0077* (2013.01); *A61B 5/7246* (2013.01);
(Continued)

(58) Field of Classification Search
CPC .......... H04N 1/00336; H04N 5/23219; G06K 9/00221; G06K 9/00335; G06K 9/46; G03B 35/00
(Continued)

(56) References Cited

U.S. PATENT DOCUMENTS 6,470,392 B1   10/2002   Murase et al.
7,184,606 B2   2/2007   Shindo et al.
(Continued)

FOREIGN PATENT DOCUMENTS

JP   2000-13775   1/2000
JP   2003-21859   1/2003
(Continued)

OTHER PUBLICATIONS

International Search Report dated Apr. 28, 2014 in International (PCT) Application No. PCT/JP2014/000758.
(Continued)

*Primary Examiner* — Xi Wang
(74) *Attorney, Agent, or Firm* — Wenderoth, Lind & Ponack, L.L.P.

(57) ABSTRACT

Provided is a digital mirror apparatus including: a camera that captures an image of a user; a display having a display surface located at a position that allows the user to visually identify the display; a controller; a memory; and a control panel operable by the user, wherein the controller: horizontally flips a live image of the user that is being captured by the camera to generate a mirror image; reads a reference image to be compared with the mirror image; superimposes the reference image on the mirror image to display on the display a display image in a region of the display in which the reference image and the mirror image overlap one another; and stores one frame of the live image in the memory, based on an operation performed on the control (Continued)

panel by the user while the display image is displayed on the display.

3 Claims, 12 Drawing Sheets

(51) Int. Cl.
| | |
|---|---|
| H04N 5/232 | (2006.01) |
| H04N 5/262 | (2006.01) |
| G06T 3/60 | (2006.01) |
| A61B 5/00 | (2006.01) |
| G06K 9/00 | (2006.01) |
| G06K 9/32 | (2006.01) |
| A61B 5/1171 | (2016.01) |

(52) U.S. Cl.
CPC ........ *A61B 5/7425* (2013.01); *G06K 9/00228* (2013.01); *G06K 9/3208* (2013.01); *G06T 3/60* (2013.01); *H04N 5/23219* (2013.01); *H04N 5/23222* (2013.01); *H04N 5/23293* (2013.01); *H04N 5/2621* (2013.01); *A61B 5/0075* (2013.01); *A61B 5/1176* (2013.01); *A61B 5/445* (2013.01); *A61B 5/7264* (2013.01); *A61B 2503/12* (2013.01)

(58) Field of Classification Search
USPC ...... 348/222.1, 239, 333.09, 333.06, 333.12; 345/629, 634; 382/118
See application file for complete search history.

(56) References Cited

U.S. PATENT DOCUMENTS

| | | | |
|---|---|---|---|
| 2003/0156199 A1 | 8/2003 | Shindo et al. | |
| 2005/0179791 A1 | 8/2005 | Iga | |
| 2006/0098112 A1* | 5/2006 | Kelly | H04N 5/23222 348/333.12 |
| 2006/0291846 A1* | 12/2006 | Hosoya | G03B 13/34 396/123 |
| 2007/0002157 A1* | 1/2007 | Shintani | H04N 5/23293 348/333.06 |
| 2008/0031495 A1 | 2/2008 | Saijo et al. | |
| 2008/0117307 A1* | 5/2008 | Sato | H04N 5/23203 348/222.1 |
| 2008/0239104 A1* | 10/2008 | Koh | G06K 9/00221 348/240.99 |
| 2010/0091135 A1* | 4/2010 | Iwamoto | G06K 9/00221 348/229.1 |
| 2010/0157128 A1* | 6/2010 | Choi | H04N 5/23248 348/333.03 |
| 2010/0188520 A1* | 7/2010 | In | H04N 5/232 348/222.1 |
| 2010/0194900 A1* | 8/2010 | Watanabe | A61B 5/1176 348/211.4 |
| 2010/0195912 A1* | 8/2010 | Nakada | G06T 11/00 382/190 |
| 2010/0328432 A1 | 12/2010 | Tanaka | |
| 2011/0074818 A1* | 3/2011 | Masuda | G06T 7/0075 345/634 |
| 2011/0128395 A1* | 6/2011 | Choi | G06K 9/00281 348/222.1 |
| 2011/0305388 A1* | 12/2011 | Wedi | G06T 5/005 382/165 |
| 2012/0092545 A1* | 4/2012 | Sugawara | G02B 7/285 348/345 |
| 2012/0162476 A1 | 6/2012 | Onoda | |
| 2012/0299949 A1 | 11/2012 | Suzuki et al. | |
| 2013/0040700 A1* | 2/2013 | Nishikawa | H04N 5/2256 455/556.1 |
| 2014/0071247 A1* | 3/2014 | Imamura | G03B 35/08 348/49 |
| 2014/0184841 A1* | 7/2014 | Woo | H04N 5/23232 348/218.1 |
| 2014/0198962 A1* | 7/2014 | Anabuki | G06T 7/0014 382/128 |
| 2015/0332087 A1* | 11/2015 | Joshi | G06K 9/00 382/203 |

FOREIGN PATENT DOCUMENTS

| | | |
|---|---|---|
| JP | 2003-189161 | 7/2003 |
| JP | 2004-302424 | 10/2004 |
| JP | 2005-117316 | 4/2005 |
| JP | 2008-54031 | 3/2008 |
| JP | 2009-53328 | 3/2009 |
| JP | 2009-61178 | 3/2009 |
| JP | 2009-176208 | 8/2009 |
| JP | 2009-188528 | 8/2009 |
| JP | 2010-219645 | 9/2010 |
| JP | 2012-142721 | 7/2012 |

OTHER PUBLICATIONS

Extended European Search Report dated Feb. 26, 2016 in European Application No. 14751139.8.
Extended European Search Report dated Jan. 12, 2017 in European Application No. 16176569.8.
Partial European Search Report dated Oct. 5, 2016 in European Application No. 16176569.8.

* cited by examiner

DIGITAL MIRROR APPARATUS

TECHNICAL FIELD

The present invention relates to a digital mirror apparatus.

BACKGROUND ART

In beauty counters, beauty care salons, cosmetic dermatologists, and others, the effect of makeup or treatment is sometimes checked by regularly examining facial information and observing the chronological changes. The facial information includes detailed information on, for example, amount of moisture, amount of oil, pores, skin texture, blemishes, wrinkles, and porphyrin, and general information on the face, such as skin sagging, skin color unevenness, facial contour, and finished makeup.

In order to evaluate the chronological changes in facial information, it is preferred that a past image and a new image should be captured under the same conditions when these images are compared. When these images are captured, differences in color and brightness of lighting, a positional relationship between the light and the face, and a positional relationship between the camera and the face may hinder accurate comparison and evaluation of these images.

In order to capture images of the face under the same conditions as much as possible, Patent Literature (hereinafter abbreviated as "PTL") 1 proposes a method for maintaining fixed positions of the face and a camera that captures images of the face, using a face holder, and evenly illuminating the face by covering the face with a light diffusion plate to eliminate the influence of ambient light. Methods focusing solely on the face orientation have also been proposed, for example, a method for detecting the parietal region of the head and determining whether the parietal region is at a reference position (see, for example, PTL 2), a method for detecting characteristic parts from the face, such as the eyes, the ears, and the nose and determining whether the characteristic parts are at respective reference positions (see, for example, PTL 3), and a method for detecting an amount of displacement between data items in a face image and reference waveform data items by comparison (see, for example, PTL 4).

CITATION LIST

Patent Literature

[PTL 1] Unexamined Patent Application Publication No. 2004-302424
[PTL 2] Unexamined Patent Application Publication No. 2003-189161
[PTL 3] Unexamined Patent Application Publication No. 2005-117316
[PTL 4] Unexamined Patent Application Publication No. 2009-188528

SUMMARY OF INVENTION

Technical Problem

The present invention provides a digital mirror apparatus that is suitable for use in comparison between previously and newly captured images and that simply and satisfactorily capture images.

Solution to Problem

A digital mirror apparatus according to an aspect of the present invention includes: a camera that captures an image of a user; a display having a display surface located at a position that allows the user whose image is captured by the camera to visually identify the display; a controller; a memory; and a control panel operable by the user, wherein the controller: horizontally flips a live image of the user that is being captured by the camera to generate a mirror image; reads a reference image to be compared with the mirror image of the live image of the user; superimposes the reference image on the mirror image of the live image to display on the display a display image in a region of the display in which the reference image and the mirror image overlap one another; and stores one frame of the live image in the memory, based on an operation performed on the control panel by the user while the display image is displayed on the display. Furthermore, a digital mirror apparatus according to another aspect of the present invention includes: a camera that captures an image of a user; a display having a display surface located at a position that allows the user whose image is captured by the camera to visually identify the display; a controller; and a memory, wherein the controller: horizontally flips a live image of the user that is being captured by the camera to generate a mirror image; reads a reference image to be compared with the mirror image of the live image of the user; and superimposes the reference image on the mirror image of the live image to display on the display a display image in a region of the display in which the reference image and the mirror image overlap one another, definition information for defining a gesture of the user and an operation of storing one frame of the live image are stored in association with each other in the memory, and the controller stores the one frame of the live image in the memory when determining that the user has made the gesture defined in the definition information stored in the memory.

A digital mirror apparatus according to another aspect of the present invention includes: a camera that captures an image of a user; a display having a display surface located at a position that allows the user whose image is captured by the camera to visually identify the display; and a controller that outputs to the display the image of the user that is captured by the camera, wherein the controller horizontally flips a live image of the user that is being captured by the camera to generate a mirror image; reads a reference image to be compared with the mirror image of the live image of the user; extracts a matching degree between the live image and the reference image, and superimpose an image indicating the extracted matching degree on the mirror image of the live image to output a display image to the display.

A digital mirror apparatus according to another aspect of the present invention includes: a camera that captures an image of a user; a display having a display surface located at a position that allows the user whose image is captured by the camera to visually identify the display; and a controller that outputs to the display the image of the user that is captured by the camera, wherein the controller: horizontally flips a live image of the user that is being captured by the camera to generate a mirror image; continuously obtains first information on at least one of a position and a face orientation of the user, based on the live image that is being captured by the camera; obtains second information on at least one of a position and a face orientation of the user in a reference image to be compared with a mirror image of the live image of the user; extracts a matching degree between the first information and the second information by comparison; and superimpose an image indicating the extracted matching degree on the mirror image of the live image to output a display image to the display.

A digital mirror apparatus according to another aspect of the present invention includes: a camera that captures an image from which parallax can be extracted; a display having a display surface located at a position that allows the user whose image is captured by the camera to visually identify the display; and a controller that outputs to the display the image captured by the camera; and a memory, wherein the controller: horizontally flips a live image of the user that is being captured by the camera to output a display image to the display; stores one frame of the live image of the user that is being captured by the camera at an imaging timing, in the memory; extracts the parallax based on an image of the user in the one frame; calculates a distance between the camera and the user based on the parallax; and stores the calculated distance and the image of the one frame in association with each other in the memory.

The general or specific aspects may be implemented by a system, a method, an integrated circuit, a computer program, or a recording medium, or by an arbitrary combination of the system, the method, the integrated circuit, the computer program, and the recording medium.

Advantageous Effects of Invention

The present invention can provide a digital mirror apparatus that is suitable for use in comparison between previously and newly captured images and that simply and satisfactorily capture images.

DESCRIPTION OF EMBODIMENTS

Figure 1:
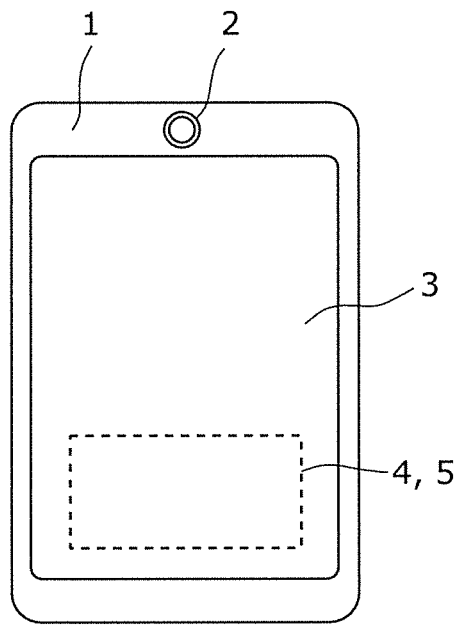
FIG. 1 illustrates an example external view of a digital mirror apparatus according to Embodiment 1 of the present invention.

A digital mirror apparatus according to an aspect of the present invention includes: a camera that captures an image of a user; a display having a display surface located at a position that allows the user whose image is captured by the camera to visually identify the display; a controller; a memory; and a control panel operable by the user, wherein the controller: horizontally flips a live image of the user that is being captured by the camera to generate a mirror image; reads a reference image to be compared with the mirror image of the live image of the user; superimposes the reference image on the mirror image of the live image to display on the display a display image in a region of the display in which the reference image and the mirror image overlap one another; and stores one frame of the live image in the memory, based on an operation performed on the control panel by the user while the display image is displayed on the display. Furthermore, a digital mirror apparatus according to another aspect of the present invention includes: a camera that captures an image of a user; a display having a display surface located at a position that allows the user whose image is captured by the camera to visually identify the display; a controller; and a memory, wherein the controller: horizontally flips a live image of the user that is being captured by the camera to generate a mirror image; reads a reference image to be compared with the mirror image of the live image of the user; and superimposes the reference image on the mirror image of the live image to display on the display a display image in a region of the display in which the reference image and the mirror image overlap one another, definition information for defining a gesture of the user and an operation of storing one frame of the live image are stored in association with each other in the memory, and the controller stores the one frame of the live image in the memory when determining that the user has made the gesture defined in the definition information stored in the memory.

Furthermore, the digital mirror apparatus may include a memory, wherein the memory may store one frame of a live image previously captured by the camera, as the reference image, and the controller may: read the reference image from the memory; and superimpose a mirror image of the reference image that is read from the memory on the mirror image of the live image to output a display image to the display.

Furthermore, the reference image may be the one frame of the live image previously captured by the camera.

Such a structure allows the user to visually check the reference image and the live image that is currently being captured by the camera simultaneously, thus supporting the simple and satisfactory alignment of the reference image and the live image when these images are compared.

Furthermore, the controller may read the reference image from an external medium, and superimpose a mirror image of the reference image that is read from the external medium on the mirror image of the live image to output a display image to the display.

Furthermore, the controller may process the reference image into a translucent reference image, and superimpose the translucent reference image on the live image to output a display image to the display.

Furthermore, the controller may extract a contour from the reference image, and superimpose an image representing the contour on the live image to output a display image to the display.

Furthermore, the controller may detect a feature point from the reference image, and superimpose an image indicating the feature point on the live image to output a display image to the display.

Such a structure can provide the user with the image information for supporting the alignment using various display modes.

Furthermore, a digital mirror apparatus according to another aspect of the present invention includes: a camera that captures an image of a user; a display having a display surface located at a position that allows the user whose image is captured by the camera to visually identify the display; and a controller that outputs to the display the image of the user that is captured by the camera, wherein the controller horizontally flips a live image of the user that is being captured by the camera to generate a mirror image; reads a reference image to be compared with the mirror image of the live image of the user; extracts a matching degree between the live image and the reference image, and superimpose an image indicating the extracted matching degree on the mirror image of the live image to output a display image to the display.

With the structure, the user can check the live image together with the matching degree between the live image and the reference image. Thus, the user can release a shutter at the timing under conditions closer to those under which the reference image is captured.

Furthermore, when each of the live image and the reference image represents a face of the user, the controller may extract the matching degree based on a sum of differences in luminance of pixels between the live image and the reference image, the pixels being located inside a facial contour of the face in each of the live image and the reference image.

Furthermore, a digital mirror apparatus according to another aspect of the present invention includes: a camera that captures an image of a user; a display having a display surface located at a position that allows the user whose image is captured by the camera to visually identify the display; and a controller that outputs to the display the image of the user that is captured by the camera, wherein the controller: horizontally flips a live image of the user that is being captured by the camera to generate a mirror image; continuously obtains first information on at least one of a position and a face orientation of the user, based on the live image that is being captured by the camera; obtains second information on at least one of a position and a face orientation of the user in a reference image to be compared with a mirror image of the live image of the user; extracts a matching degree between the first information and the second information by comparison; and superimpose an image indicating the extracted matching degree on the mirror image of the live image to output a display image to the display.

With the structure, the user can check the live image together with the matching degree between the live image and the reference image. Thus, the user can release a shutter at the timing under conditions closer to those under which the reference image is captured.

Furthermore, the digital mirror apparatus may include a memory, wherein the memory may store the second information on at least one of the position and the face orientation of the user in the reference image, using one frame of a live image previously captured by the camera as the reference image, the controller may read the second information from the memory, and extract a matching degree between the first information and the second information read from the memory, by comparison.

Furthermore, a digital mirror apparatus according to another aspect of the present invention includes: a camera that captures an image from which parallax can be extracted; a display having a display surface located at a position that allows the user whose image is captured by the camera to visually identify the display; and a controller that outputs to the display the image captured by the camera; and a memory, wherein the controller: horizontally flips a live image of the user that is being captured by the camera to output a display image to the display; stores one frame of the live image of the user that is being captured by the camera at an imaging timing, in the memory; extracts the parallax based on an image of the user in the one frame; calculates a distance between the camera and the user based on the parallax; and stores the calculated distance and the image of the one frame in association with each other in the memory.

With the structure, the user can compare and evaluate previously and newly captured images based on the distance information even when imaging conditions of these images are different.

Furthermore, the memory may store definition information for defining gestures of the user, the controller may determine whether or not the user in the live image has made a gesture defined in the definition information stored in the memory, and store one frame of the live image when it is determined that the user has made the gesture.

Such a structure allows the user to operate the digital mirror apparatus without directly touching it, thus increasing the user's convenience.

Furthermore, the memory may store data of a color sample, and the controller may adjust the color balance of the live image based on the data of the color sample stored in the memory.

Such a structure enables provision of the digital mirror apparatus that can support not only the alignment but also the color matching when the reference image and the live image are compared.

The general or specific aspects may be implemented by a system, a method, an integrated circuit, a computer program, or a recording medium, or by an arbitrary combination of the system, the method, the integrated circuit, the computer program, and the recording medium.

Embodiments of a digital mirror apparatus according to the present invention will be described with reference to the drawings.

Embodiments described hereinafter indicate preferable and specific examples of the present invention. The values, shapes, materials, constituent elements, positions and connections of the constituent elements, steps, and orders of the steps indicated in Embodiments are examples, and do not limit the present invention. The constituent elements in Embodiments that are not described in independent claims that describe the most generic concept of the present invention are described as arbitrary constituent elements.

Embodiment 1

FIG. 1 illustrates an example external view of a digital mirror apparatus 1 according to Embodiment 1. The digital mirror apparatus 1 includes a camera 2 that captures an image of a user, and a display 3. A live image of a user that is captured by the camera 2 can be displayed on the display 3. The live image is video represented by a series of still frames (simply referred to as "frames" or "pictures"). One frame of a live image may be called a live image in the following Description. The display 3 has a display surface located at a position that allows the user whose image is captured by the camera to visually identify the display. The digital mirror apparatus 1 includes a memory 4 and a controller 5 inside the enclosure.

Figure 2:
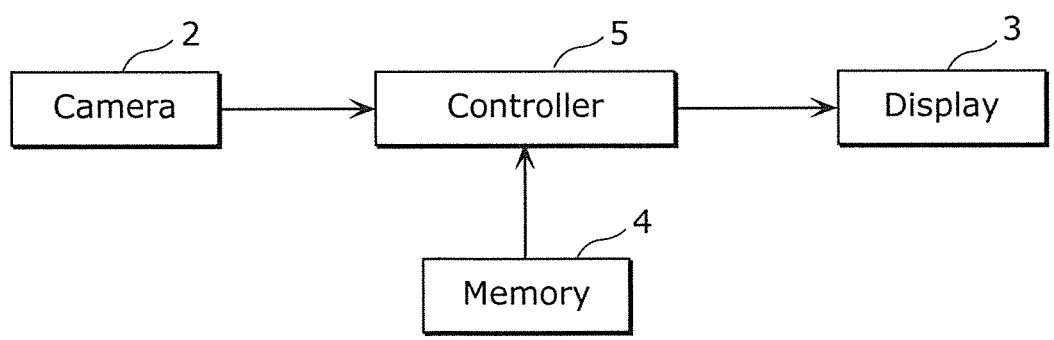
FIG. 2 is a block diagram illustrating an example of a functional configuration of the digital mirror apparatus according to Embodiment 1.

FIG. 2 is a block diagram illustrating an example of a functional configuration of the digital mirror apparatus 1 according to Embodiment 1.

The memory 4 stores a reference image to be compared with an image of the user that is captured by the camera 2. The reference image may be, for example, one frame of a live image previously captured by the camera 2. The reference image can be called up from the memory 4 and displayed on the display 3.

The controller 5 superimposes the reference image stored in the memory 4 on the live image obtained by the camera 2 through image processing such as reverse, rotation, and color correction to output a display image. The display image can be displayed on the display 3.

Furthermore, the controller 5 reads the reference image from the memory 4. The reference image may be read from the controller 5 or an external medium. The controller 5 superimposes a mirror image of the reference image that is read from the memory 4 or another external medium on a mirror image of the live image to output a display image. The display image can be output to and displayed on the display 3.

Examples of how the digital mirror apparatus 1 is used will be described with reference to FIGS. 3 and 4. To simplify the description of the mirror image, not the face but the hand of the user is used in the drawings.

Figure 3:
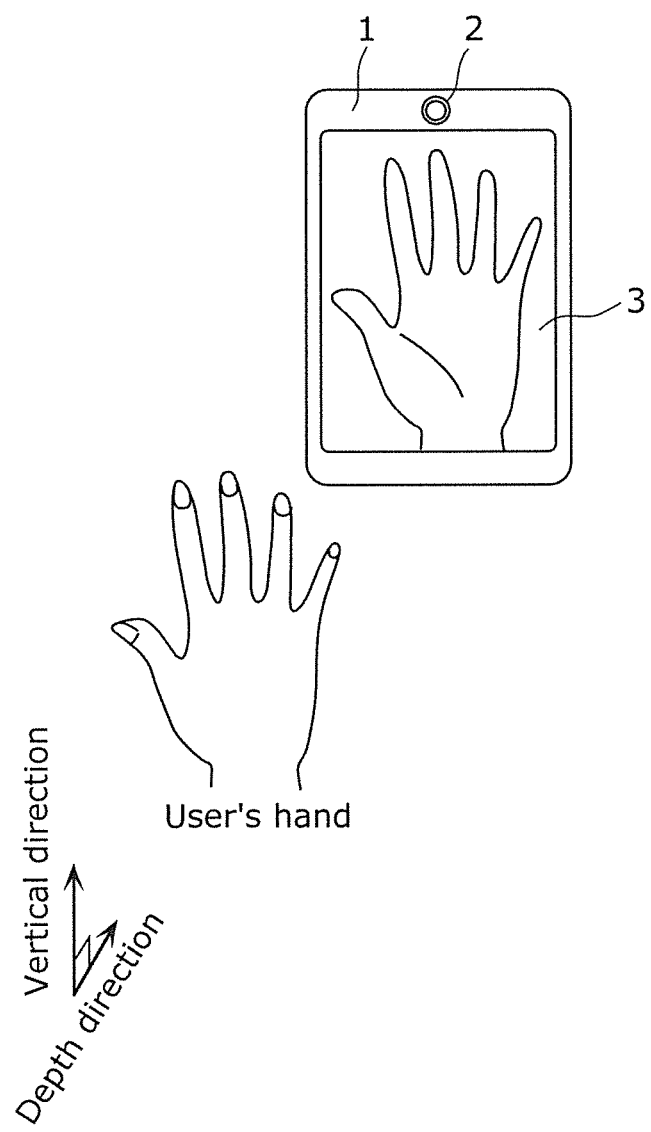
FIG. 3 schematically illustrates an example of how the digital mirror apparatus according to Embodiment 1 is used.

FIG. 3 schematically illustrates a positional relationship between the digital mirror apparatus 1 and the user, assuming that the user is closer to the viewer of FIG. 3 and the digital mirror apparatus 1 is distant from the viewer.

Figure 4:
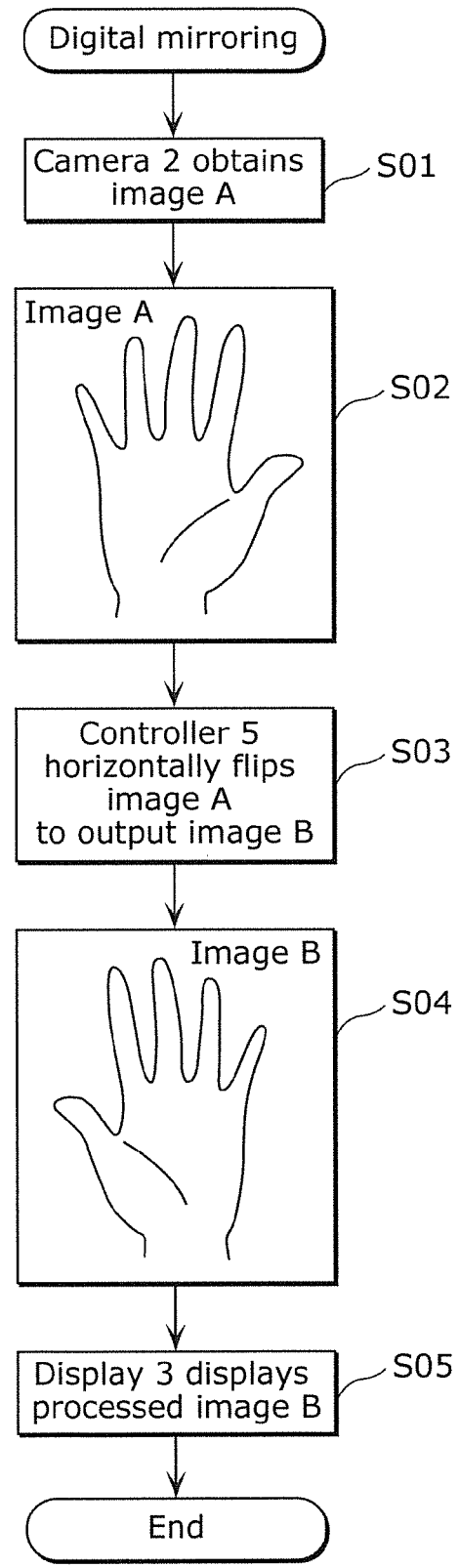
FIG. 4 is a flowchart of an example of basic operations performed by the digital mirror apparatus according to Embodiment 1.

FIG. 4 is a flowchart of an example of basic operations performed by the digital mirror apparatus 1.

As indicated in FIG. 4, the camera 2 obtains an image A of the user (S01, S02), the controller 5 horizontally flips the image A to output an image B to the display 3 (S03, S04), and the display 3 displays the image B (S05). During repetition of such processes, the images A and B form one frame of the live image of the user. The images A and B can be stored in the memory 4, and printed, transmitted in data, and can be moved to an external memory.

The user stores, in the memory 4, one frame that is preferred by the user as a reference image, while visually checking the live image. The reference images previously stored in the memory 4 can be called up to be compared with the image of the user in the live image that is currently being captured.

Figure 5:
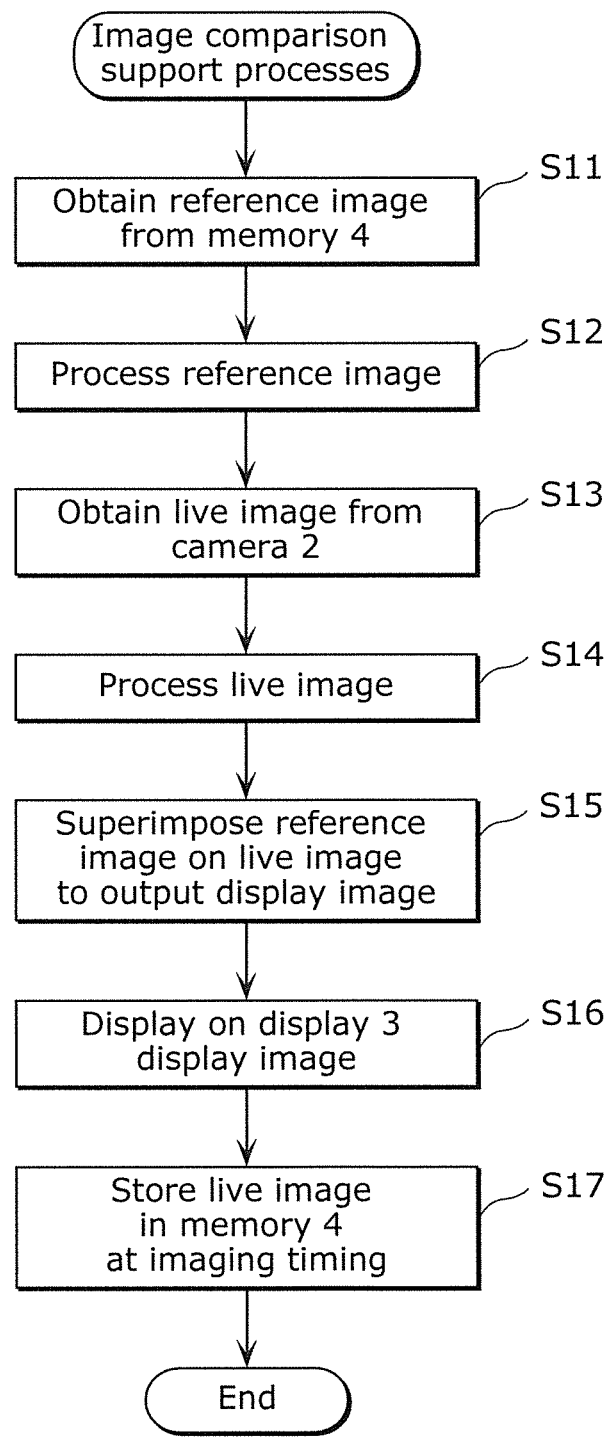
FIG. 5 is a flowchart of an example of detailed operations performed by the digital mirror apparatus according to Embodiment 1.

Next, characteristic support operations to be performed by the digital mirror apparatus 1 will be described based on the display example in FIG. 6 with reference to the flowchart in FIG. 5 to enable the user to easily compare the image of the user between the reference image and the live image that is being captured.

The controller 5 obtains a reference image stored in the memory 4 (S11). The reference image may be, for example, an image previously captured by the camera 2 and stored in the memory 4. The controller 5 processes the obtained reference image (S12). The processing on the reference image may include image reduction and horizontal flipping.

The controller 5 obtains the live image of the user that is currently being captured by the camera 2 (S13). The frame rate of the live image may be, but not limited to, approximately several to several tens of frames as a practical example. The controller 5 processes the obtained live image (S14). The processing on the live image may include image reduction, horizontal flipping, and color correction.

The controller 5 superimposes a mirror image of the reference image on a mirror image of the live image (S15) to display a display image on the display 3 (S16). The method for superimposing the image is not limited. For example, the controller 5 may superimpose the reference image on the live image to be displayed simultaneously, to display a display image in a region of the display 3 in which the reference image and the live image do not overlap one another.

Figure 6:
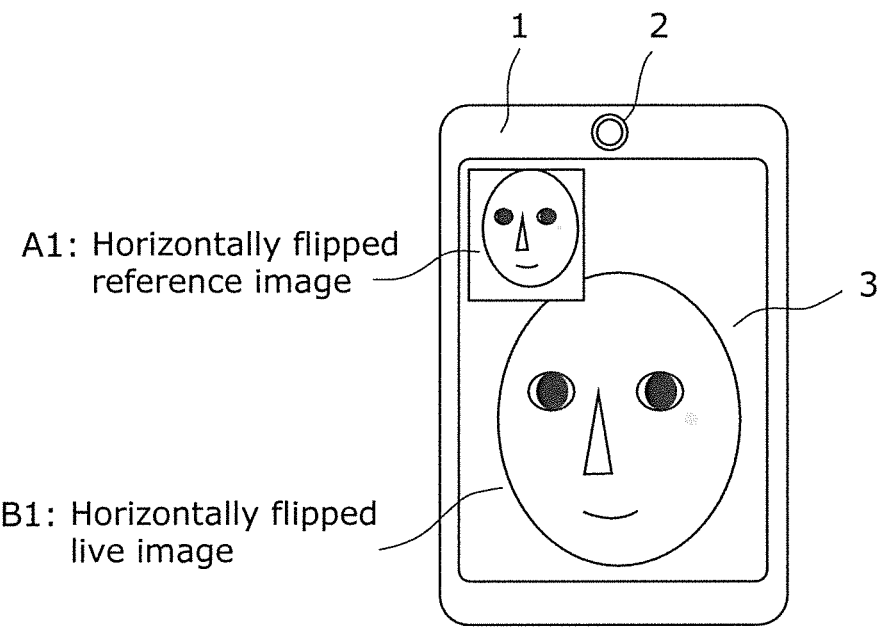
FIG. 6 illustrates a display example of the digital mirror apparatus according to Embodiment 1.

As exemplified in FIG. 6, a reference image A1 horizontally flipped and reduced may be displayed in a small region to the upper left of the display 3, whereas a live image B1 horizontally flipped may be displayed in the remaining region other than the small region of the display 3.

The user can adjust the face orientation by viewing the display image displayed on the display 3, and store one frame of the live image B1 in the memory 4 when the face orientation of the reference image A1 is identical to that of the live image B1 (S17).

As such, the digital mirror apparatus 1 can support simple and satisfactory alignment when the reference image and the live image are compared.

The control panel (not illustrated) of the digital mirror apparatus 1 may be of contact type, such as a button or a touch panel, but of contactless type. Human sensors or image processing techniques may be used for operating the control panel contactlessly. For example, definition information for defining gestures of the user and operations of the digital mirror apparatus 1 (for example, an operation of storing one frame of a live image) may be in advance stored in association with each other in the memory 4, and the digital mirror apparatus 1 may perform an associated operation when it is determined that the user makes the gesture defined in the stored definition information.

The methods for contactlessly operating the control panel by gesture produce, for example, the following advantages.

For example, when the user applies makeup while looking at the digital mirror apparatus 1, if the user operates the control panel of contact type with a stain left on the hand, the stain may be adhered to the control panel. Using the method for contactlessly operating the control panel by gesture can prevent the control panel from being stained.

Furthermore, porphyrin or hidden blemishes may be observed by irradiating the skin with ultraviolet rays to obtain, for example, skin condition information. However, the ultraviolet rays may damage the cornea or the conjunctiva. In order to prevent the damage to the eyes, several seconds after the user performs a gesture of closing the eyes, the light source of the ultraviolet rays may be turned ON and images of the user that are captured in such a manner may be stored. The duration during which the user closes the eyes that is a gesture for causing the camera to start to capture the images may be set longer than the blinking. Furthermore, the user can be informed by voice of a countdown until start of storing images and of a cue for ending capturing of the images, such as a shutter sound. The methods for contactlessly operating the control panel by gesture are useful in such cases.

Furthermore, adjustment of the color balance through the digital mirror apparatus 1 may reduce the influence of color and brightness of lighting on the images, and thus facilitate the comparison between the past skin tones and the current skin tones. The color balance may be adjusted by storing color sample data in the digital mirror apparatus 1, and capturing images of an entity that corresponds to the color sample data by the camera 2.

Figure 7:
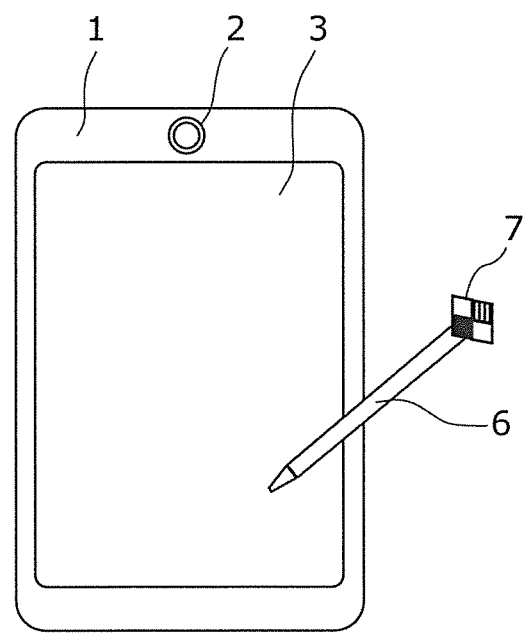
FIG. 7 illustrates an external view of the digital mirror apparatus according to Embodiment 1.

As illustrated in FIG. 7, a dedicated touch pen 6 with a color sample 7 that is provided to the digital mirror apparatus 1 allows the user to easily capture an image of the color sample 7 and adjust the color balance. The color sample data corresponding to the color sample 7 is pre-stored in the memory 4. The color sample data can reduce the inconvenience for causing the user to feel that he/she takes the trouble to, for example, capture images after preparing color samples such as color charts.

The reference image does not necessarily have to be read from the memory 4 in the digital mirror apparatus 1. For example, the controller 5 may read the reference image from an external medium. Examples of the reference image include an image captured by a camera other than the camera 2 of the digital mirror apparatus 1, an illustration indicating positions of feature points of at least one of the facial contour, the eyes, the nose, and the mouth of a face that imitates a human face, and a sample image of a makeup appeared in a magazine or an Internet site. Furthermore, the digital mirror apparatus 1 may have, at the edge, a structure for physical connection with an external medium from which the reference image is read. Furthermore, the reference image may be wirelessly read from an external medium.

Embodiment 2

Figure 8:
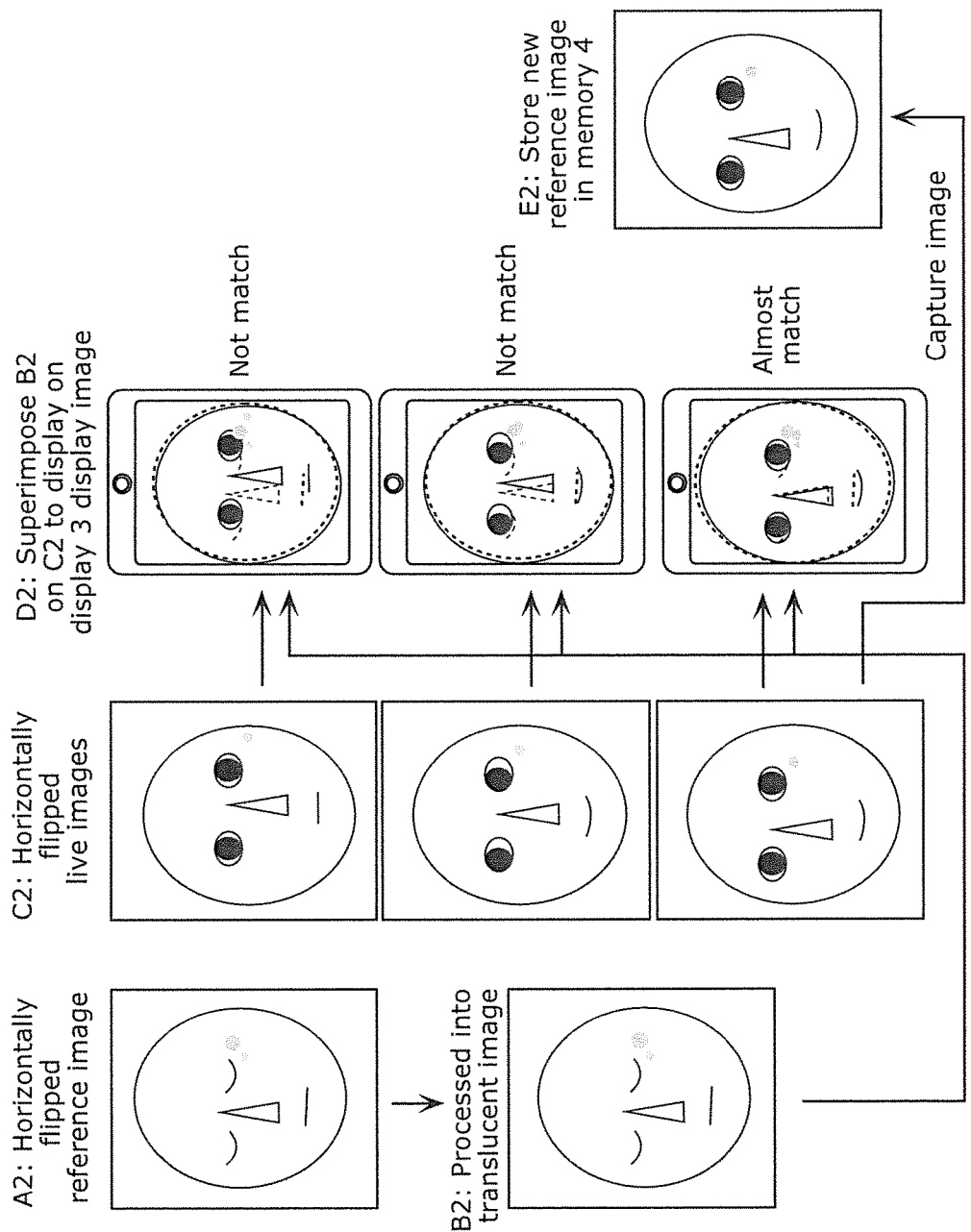
FIG. 8 illustrates display examples of a digital mirror apparatus according to Embodiment 2 of the present invention.

Embodiment 2 is different from Embodiment 1 in method for processing and displaying an image. Embodiment 2 will be hereinafter described with reference to FIG. 8.

A reference image A2 obtained in the method described above and previously horizontally flipped is called up, and is processed into a reference image B2 that is translucent. The translucent reference image B2 is superimposed on live images C2 that are being captured by the camera 2 to output display images D2. The display images D2 are displayed each in a region of the display 3 in which the translucent reference image B2 and the live image C2 overlap one another.

Here, each of the display images D2 is an example of a display image for displaying a mirror image of the live image and the reference image, in the region of the display 3 in which the translucent reference image B2 and the live image C2 overlap one another, that is, an example of a display image in which an mirror image of the user in the live image and the reference image are disposed in the region.

The user uses the translucent reference image B2 included in the display image D2 as a guide for determining the face orientation, and adjusts a distance and a positional relationship between the camera 2 and the user for matching the face orientations. When it is determined that the face orientations match, one frame of a live image C2 can be stored as a new reference image E2.

Embodiment 3

Figure 9:
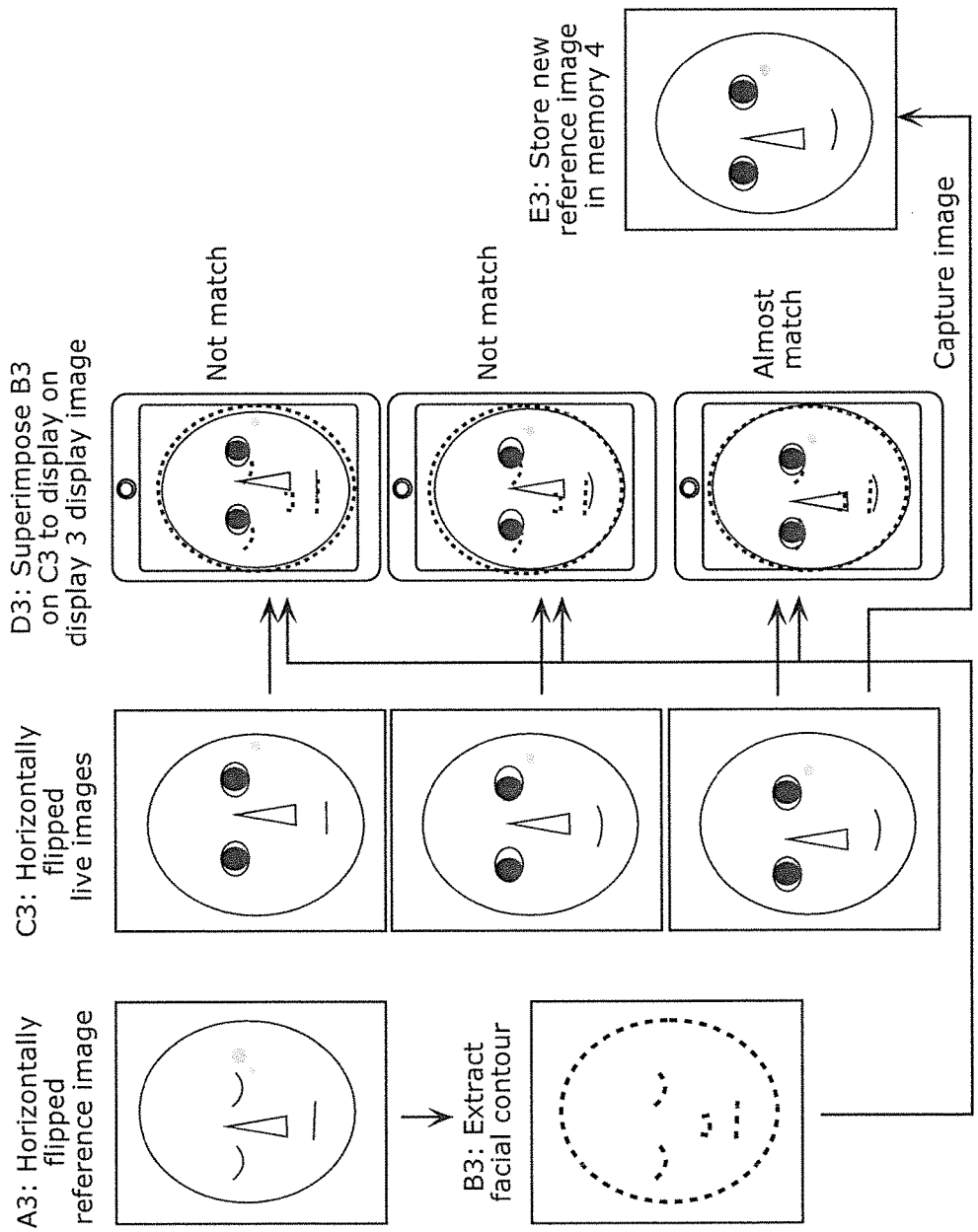
FIG. 9 illustrates display examples of a digital mirror apparatus according to Embodiment 3 of the present invention.

Embodiment 3 is different from Embodiments 1 and 2 in method for processing an image. Embodiment 3 will be hereinafter described with reference to FIG. 9.

A reference image A3 previously horizontally flipped is called up, and processed into a reference image B3 only having a facial contour extracted from the reference image A3. The reference image B3 only with the facial contour is superimposed on live images C3 that are being captured by the camera 2 to output display images D3. Each of the display images D3 is displayed in a region of the display 3 in which the reference image B3 and the live image C3 overlap one another.

Here, the display image D3 is an example of a display image for displaying the mirror image of the live image and the reference image in the region of the display 3 in which the reference image B3 and the live image C3 overlap one another, that is, an example of a display image in which an mirror image of the user in the live image and the reference image are disposed in the region.

The user uses the reference image B3 only having the facial contour that is included in the display image D3 as a guide for determining the face orientation, and adjusts a distance and a positional relationship between the camera 2 and the user for matching the face orientations. When it is determined that the face orientations match, one frame of the live image C3 can be stored as a new reference image E3.

Here, the facial contour is not limited to an outer contour of a face but also contours of the other parts, such as the eyes, the nose, and the mouth of the face. The contour may be extracted using edge detection or by simply binarizing an image and adjusting contrast and brightness of the image. The user can freely set, for example, a threshold in any of the image processing. Furthermore, the user may trace the image for extracting the contour. The present invention emphasizes the usability of the user, and does not particularly require accuracy in the image processing.

Embodiment 4

Embodiment 4 is different from Embodiments 1 to 3 in method for processing an image. Embodiment 4 will be hereinafter described with reference to FIG. 10.

A reference image A4 previously horizontally flipped is called up, and processed into a reference image B4 only having feature points extracted from the reference image A4. The reference image B4 only having the feature points is superimposed on live images C4 that are being captured by the camera 2 to output display images D4. Each of the display images D4 is displayed in a region of the display 3 in which the reference image B4 and the live image C4 overlap one another.

Here, the display image D4 is an example of a display image for displaying the mirror image of the live image and the reference image in the region of the display 3 in which the reference image B4 and the live image C4 overlap one another, that is, an example of a display image in which an mirror image of the user in the live image and the reference image are disposed in the region.

The user uses the reference images B4 only having the feature points in the display images D4 as a guide for determining the face orientation, and adjusts a distance and a positional relationship between the camera 2 and the user for matching the face orientations. When it is determined that the face orientations match, one frame of the live image C4 can be stored as a new reference image E4.

Figure 10:
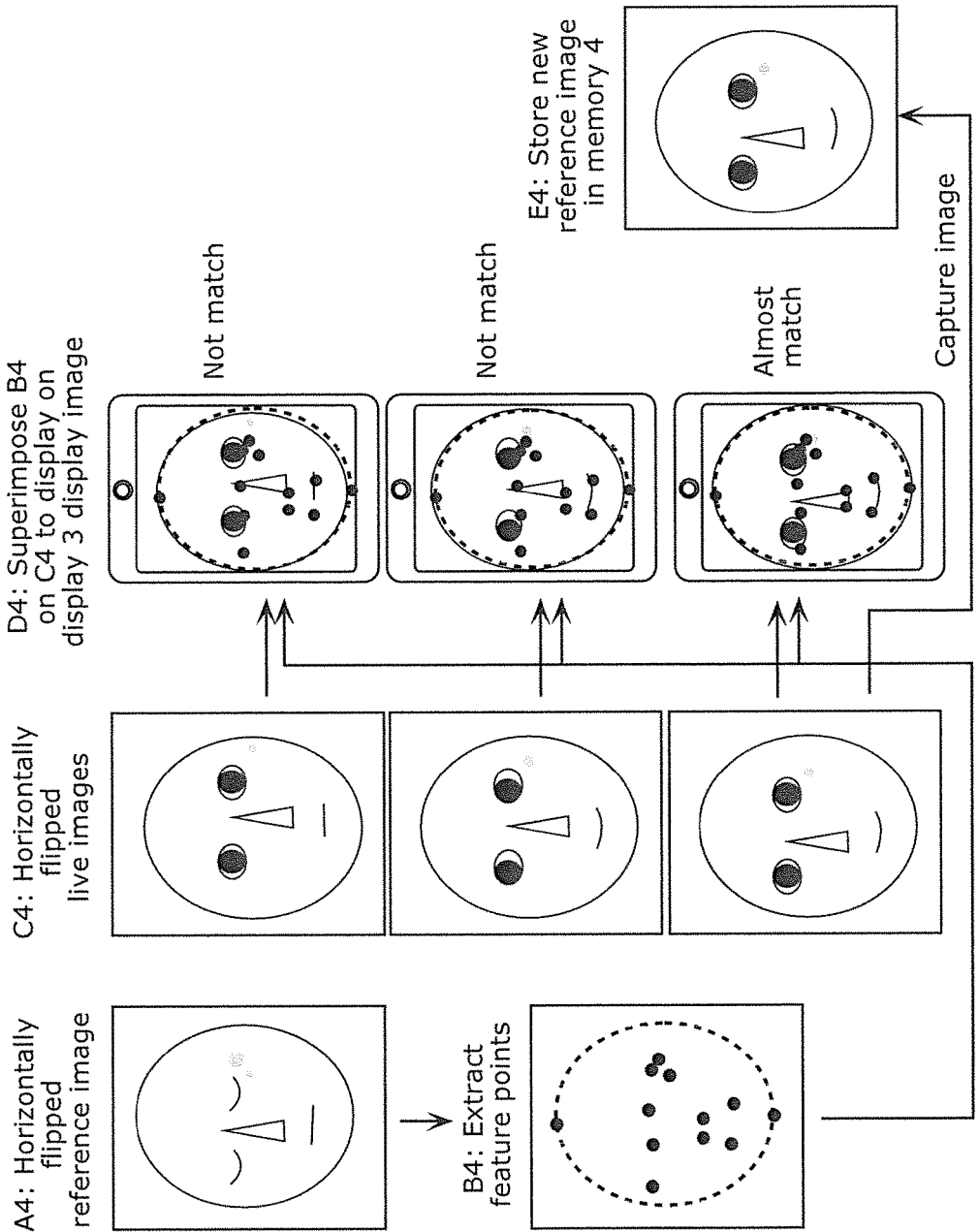
FIG. 10 illustrates display examples of a digital mirror apparatus according to Embodiment 4 of the present invention.

Here, the feature points include not only the eyes, the nose, the mouth, and the facial contour but also parts that the user desires to chronologically observe, such as blemishes and pimples. FIG. 10 illustrates an example of the feature points in the head, the chin, the inner and outer canthus, the nostrils, the angle of mouth, and a pigmentation part around the right eye, all of which are marked by black circles. The definitions of the feature points are not limited to these.

Although the feature points may be automatically extracted based on an algorism, the user may designate the feature points by tracing the image.

Embodiment 5

A digital mirror apparatus according to Embodiment 5 extracts a matching degree between a reference image previously captured by a camera 2 and a live image currently being captured thereby, by comparison. The image indicating the extracted matching degree is displayed on the display 3 together with the live image. Specifically, Embodiment 5 differs from Embodiments 1 to 4 in that the image to be displayed on the display 3 together with the live image is the image indicating the matching degree between the reference image and the live image.

A memory 4 stores a reference image to be compared with a live image of the user captured by the camera 2. The reference image may be, for example, one frame of a live image previously captured by the camera 2.

Figure 11:
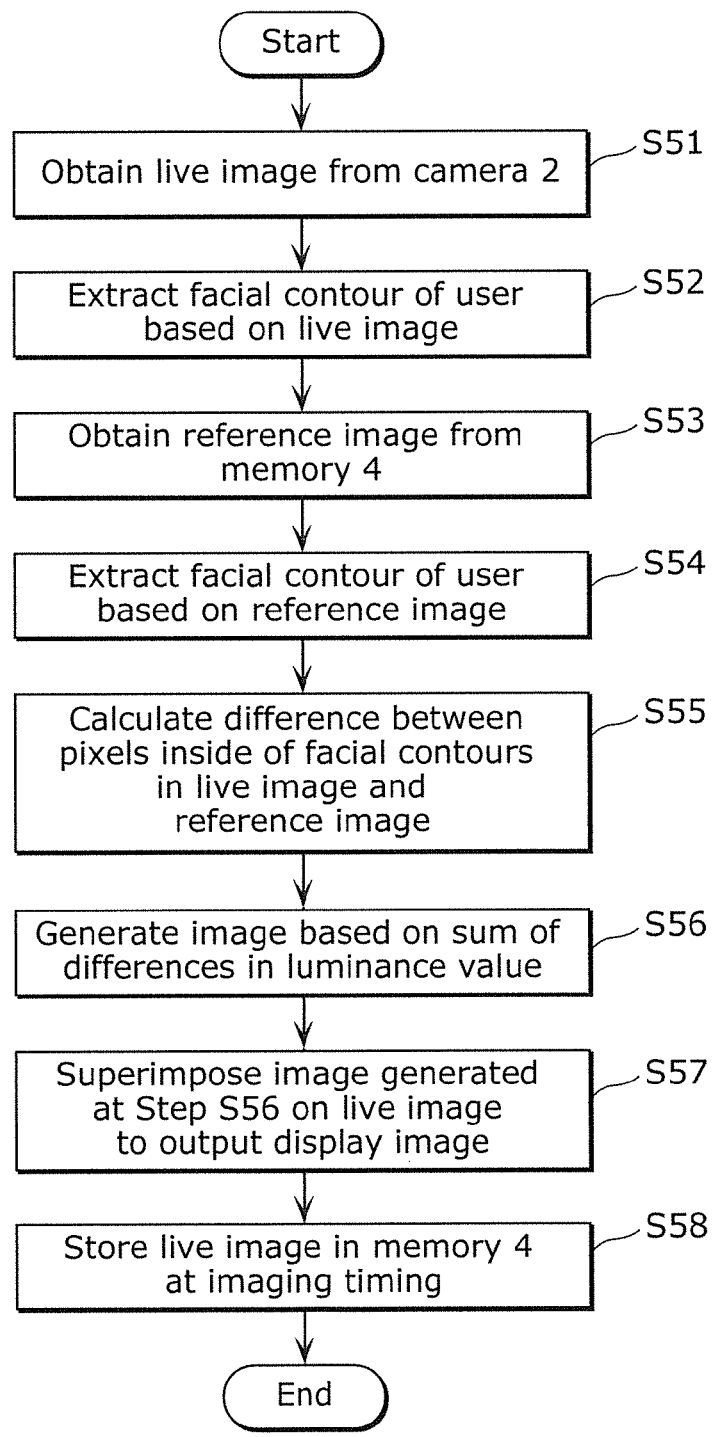
FIG. 11 is a flowchart of example detailed operations performed by a digital mirror apparatus according to Embodiment 5 of the present invention.

Operations of a controller 5 according to Embodiment 5 will be hereinafter described with reference to FIG. 11.

The controller 5 extracts a facial contour of the user based on a live image of the user that is being captured by the camera 2 (S51, S52). Furthermore, the reference image to be compared with the live image is called up from the memory 4, and the facial contour of the user in the reference image is extracted (S53, S54). Differences in luminance value between pixels inside of the facial contours in the live image and extracted from the reference image are calculated, and a sum of the differences is calculated (S55). Based on the calculated sum of the differences in luminance value, an image indicating the matching degree between the live image and the reference image of the user is generated (S56). The generated image indicating the matching degree is superimposed on a mirror image of the live image that is being captured by the camera 2 to output a display image (S57).

With the structure, the user can check the live image together with the matching degree with the reference image. Thus, the user can release a shutter at the imaging timing for obtaining a live image that is closer in conditions under which the reference image is captured, that is, a live image that is more suitable for use in comparison with the reference image (S58).

Figure 12:
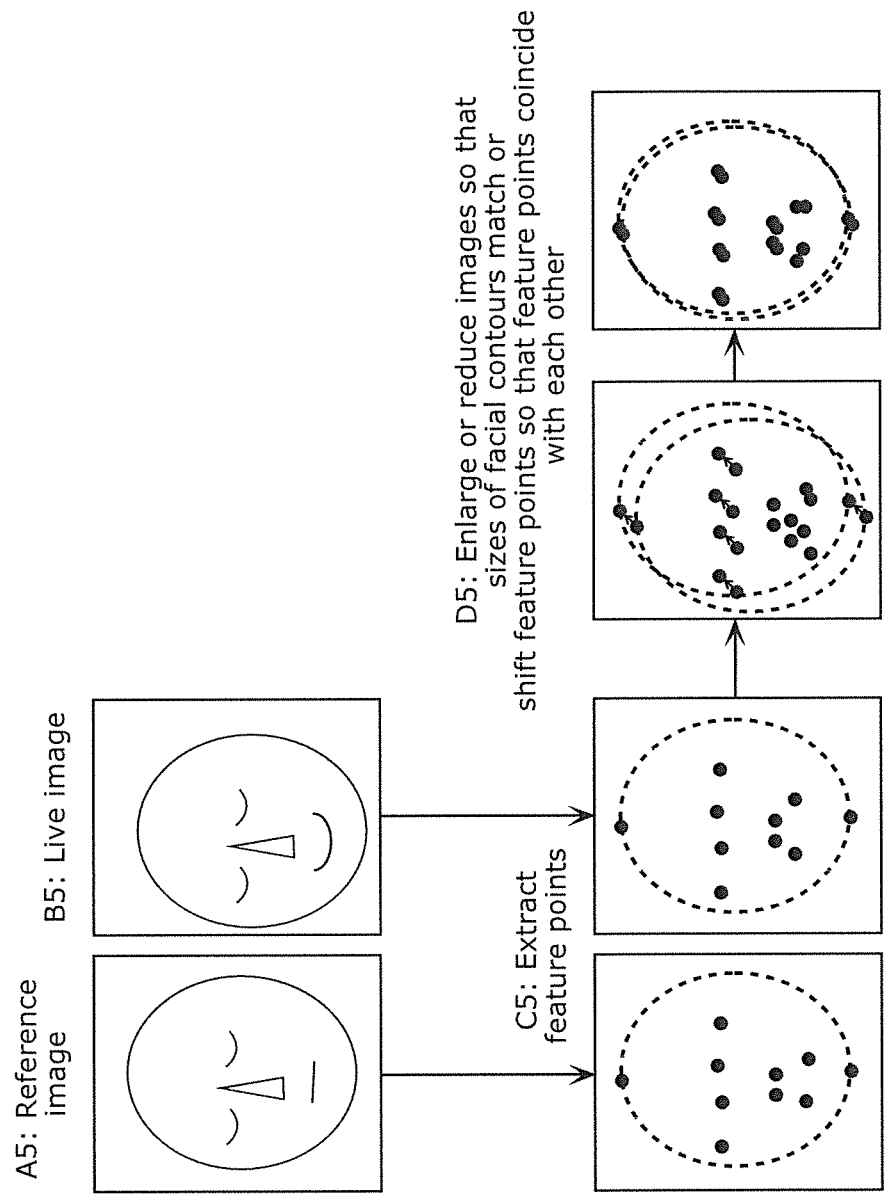
FIG. 12 illustrates an example of detailed operations performed by the digital mirror apparatus according to Embodiment 5.

When the differences in luminance value are calculated for each of the pixels in both the live image and the reference image, the pixels can be more accurately compared by enlarging or reducing the live image and the reference image so that the size of the facial contour to be extracted or positions of the feature points are identical between the live image and the reference image. Thus, when the feature points are extracted from each of the live image and the reference image (A5, B5, and C5 in FIG. 12) and the sizes of the facial contour are different between the live image and the reference image, at least one of the live image and the reference image may be enlarged or reduced so that the size of the facial contour matches between the live image and the reference image. Furthermore, when the positions of the feature points are different between the live image and the reference image, at least one set of the positions may be shifted so that the feature points coincide with each other (D5 in FIG. 12).

The image indicating the matching degree that is calculated from the differences in luminance value may be an image displayed by digitizing or graphing the sum of the differences in luminance value for each of the pixels inside of the facial contours that are, for example, in the live image and extracted from the reference image. As long as the user can check a matching degree between a frame of a live image and a reference image, these are not limited to the description above.

Although Embodiment 5 describes the calculation of the differences in luminance value between pixels inside of the facial contours that are in the live image and extracted from the reference image, the method is not limited to this. For example, a sum of luminance values of pixels inside the facial contour in the live image may be calculated, then, a sum of luminance values of pixels inside the facial contour in the reference image may be calculated, and a difference between the calculated sums of the luminance values may be calculated.

Embodiment 6

A digital mirror apparatus according to Embodiment 6 compares a position or a face orientation of the user between a reference image previously captured by the camera 2 and a live image currently being captured, and extracts a matching degree between these images. The image indicating the extracted matching degree is displayed on the display 3 together with the live image. In other words, Embodiment 6 differs from Embodiments 1 to 4 in that the image to be displayed on the display 3 together with the live image is the image indicating the matching degree between the reference image and the live image.

The memory 4 stores second information on the position or the face orientation of the user in the reference image that is to be compared with the live image of the user captured by the camera 2. The reference image may be, for example, one frame of a live image previously captured by the camera 2.

Furthermore, the memory 4 may store a reference image per se to be compared with a live image of the user. Here, the controller 5 may read the reference image from the memory 4, and calculate the second information on the position or the face orientation of the user in the reference image.

Figure 13:
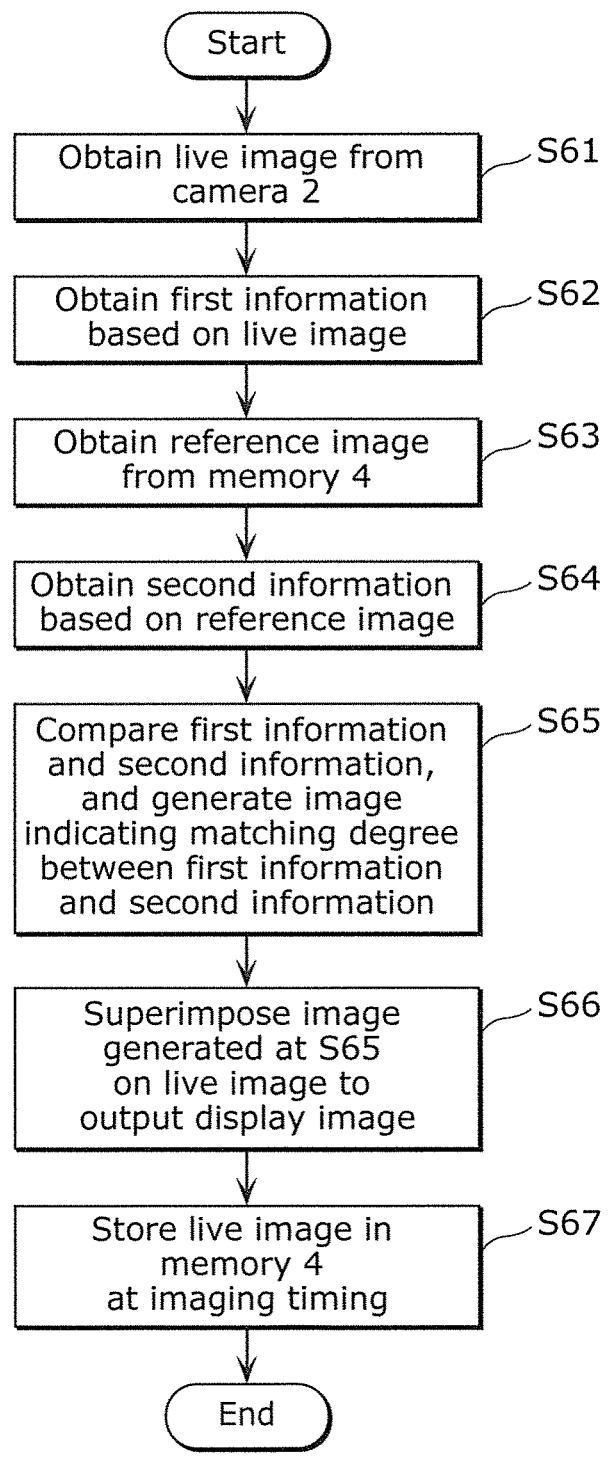
FIG. 13 is a flowchart of an example of detailed operations performed by a digital mirror apparatus according to Embodiment 6 of the present invention.

Operations of the controller 5 according to Embodiment 6 will be hereinafter described with reference to FIG. 13.

The controller 5 can continuously obtain first information on a position or a face orientation of the user based on the live image of the user that is being captured by the camera 2 (S61, S62).

Furthermore, the controller 5 can call up (or calculate) the second information from the memory 4, and compare it with the first information (S63, S64). Then, a matching degree between the first information and the second information is extracted by comparison. The extracted image indicating the matching degree is superimposed on a mirror image of the live image that is being captured by the camera 2 to output a display image (S65, S66).

With the structure, the user can check the live image together with the matching degree with the reference image. Thus, the user can release a shutter at the imaging timing for obtaining a live image that is closer in conditions under which the reference image is captured, that is, more suitable for use in comparison with the reference image (S67).

Although each of the first information and the second information is described as the information on a position or a face orientation of the user, it may be information on both a position and a face orientation of the user.

The information on a position of the user is obtained by measuring a distance from the camera 2 to the user. The distance can be measured by using the ranging technology with parallax, such as a compound-eye camera.

The face orientation of the user can be obtained by, for example, estimating a direction of a plane obtained by linking the feature points, based on the positions of the feature points of the face in an image that is being captured. Otherwise, the face orientation can be obtained by using known techniques.

The image indicating the matching degree between the first information and the second information may be an image displayed by digitizing or graphing differences between the first information and the second information. As long as the user can check the matching degree between the first information and the second information, the image is not limited to the ones above.

Embodiment 7

In the digital mirror apparatus according to Embodiment 7, a camera 2 can capture an image from which parallax can be extracted, for example, by a compound-eye camera. Furthermore, a distance between the camera 2 and the user is calculated based on the parallax in the image captured by the camera 2, and stored.

Figure 14:
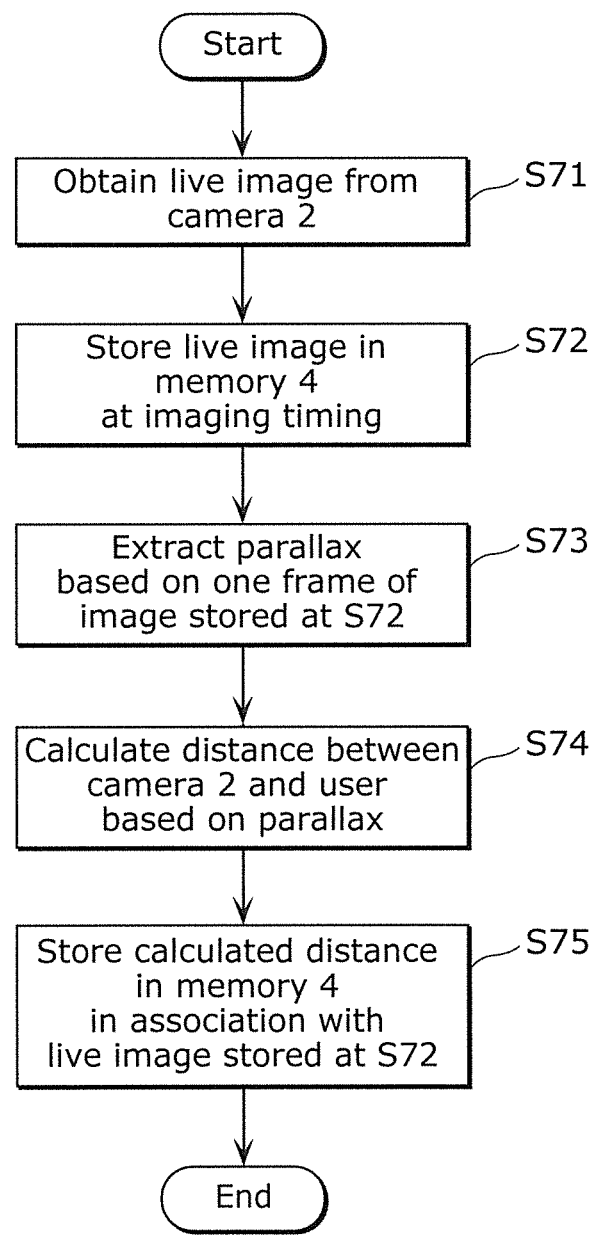
FIG. 14 is a flowchart of an example of detailed operations performed by a digital mirror apparatus according to Embodiment 7 of the present invention.

Operations of a controller 5 according to Embodiment 7 will be hereinafter described with reference to FIG. 14.

The controller 5 stores one frame of a live image of the user that is being captured by a camera at an imaging timing (S71, S72). Then, parallax is extracted based on the one frame stored in the memory 4 (S73). Then, a distance between the camera 2 and the user is calculated based on the extracted parallax, and stored in association with the captured image in the memory 4 (S74, S75). The operations are performed each time an image is captured. Accordingly, the user can estimate, for example, the number of pixels corresponding to the blemishes or the pores in the captured image, and an actual area of the blemishes or the pores based on the stored distance information. Thus, even when an image previously captured differs from an image newly captured in imaging conditions, they can be compared and evaluated based on the distance information.

In Embodiments 1 to 7, each of the constituent elements may be implemented by dedicated hardware or by executing a software program appropriate for the constituent element. Each of the constituent elements may be implemented by a program executing unit, such as a central processing unit (CPU) and a processor, reading and executing the software program recorded on a recording medium, such as a hard disk or a semiconductor memory.

Although the digital mirror apparatus according to one or more aspects of the present invention are described based on Embodiments 1 to 7, the present invention is not limited to these Embodiments. Without departing from the scope of the present invention, the aspects of the present invention include an embodiment with some modifications on Embodiments that are conceived by a person skilled in the art, and another embodiment obtained through combinations of the constituent elements of Embodiments.

For example, the subject of the digital mirror apparatus according to the present invention may be other than a human face, and the digital mirror apparatus is effective at observing chronological changes in parts other than the face, in other animals and plants, or even in non-living materials.

INDUSTRIAL APPLICABILITY

The digital mirror apparatus according to the present invention is applicable to, for example, skin diagnosis systems.

REFERENCE SIGNS LIST

1 Digital mirror apparatus
2 Camera
3 Display
4 Memory
5 Controller
6 Touch pen
7 Color sample

The invention claimed is:

1. A digital mirror apparatus, comprising:
a camera that captures an image of a user;
a display having a display surface located at a position that allows the user whose image is captured by the camera to visually identify the display;
a controller that outputs to the display the image of the user that is captured by the camera; and
a memory that stores definition information for defining a gesture of the user,
wherein the controller horizontally flips a live image of the user that is being captured by the camera to generate a mirror image; reads a reference image, the reference image being an image of the user previously captured by the camera; compares the reference image with the mirror image of the live image of the user and extracts a matching degree between (i) a distance from the camera to the user and a face orientation of the user in the live image and (ii) a distance from the camera to the user and a face orientation of the user, respectively, in the reference image, and superimposes an image indicating the extracted matching degree on the mirror image of the live image to output a display image to the display,
wherein when each of the live image and the reference image represents a face of the user, the controller extracts the matching degree based on a sum of differences in luminance of pixels between the live image and the reference image,
wherein the image indicating the extracted matching degree is an image displayed by digitizing or graphing the differences in luminance value, and
wherein the controller determines whether or not the user in the live image has made a gesture defined in the definition information stored in the memory, and stores one frame of the live image when it is determined that the user had made the gesture.

2. A digital mirror apparatus, comprising:
a camera that captures an image of a user;
a display having a display surface located at a position that allows the user whose image is captured by the camera to visually identify the display;
a controller that outputs to the display the image of the user that is captured by the camera; and
a memory that stores definition information for defining a gesture of the user,
wherein the controller:
horizontally flips a live image of the user that is being captured by the camera to generate a mirror image;

continuously obtains first information on a distance from the camera to the user and a face orientation of the user, based on the live image that is being captured by the camera;

obtains second information on a distance from the camera to the user and a face orientation of the user in a reference image to be compared with a mirror image of the live image of the user, the reference image being an image of the user previously captured by the camera;

compares the reference image with the mirror image of the live image of the user and extracts a matching degree between the first information and the second information by comparison; and superimposes an image indicating the extracted matching degree on the mirror image of the live image to output a display image to the display, wherein when each of the live image and the reference image represents a face of the user, the controller extracts the matching degree based on a sum of differences in luminance of pixels between the live image and the reference image, wherein the image indicating the extracted matching degree is an image displayed by digitizing or graphing the differences in luminance value, and wherein the controller determines whether or not the user in the live image has made a gesture defined in the definition information stored in the memory, and stores one frame of the live image when it is determined that the user had made the gesture.

3. The digital mirror apparatus according to claim 2, further comprising a memory, wherein the memory stores the second information on the distance from the camera to the user and the face orientation of the user in the reference image, using one frame of a live image previously captured by the camera as the reference image, the controller reads the second information from the memory, and extracts a matching degree between the first information and the second information read from the memory, by comparison.

* * * * *